(12) United States Patent
Yuan et al.

(10) Patent No.: US 6,831,155 B2
(45) Date of Patent: Dec. 14, 2004

(54) INHIBITION OF P53 DEGRADATION

(75) Inventors: Zhi-Min Yuan, Newton, MA (US); JiJie Gu, Newton, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 09/732,384

(22) Filed: Dec. 7, 2000

(65) Prior Publication Data

US 2002/0132977 A1 Sep. 19, 2002

Related U.S. Application Data

(60) Provisional application No. 60/169,816, filed on Dec. 8, 1999.

(51) Int. Cl.$^7$ .................... C07K 14/00; C07K 19/00; A61K 38/17
(52) U.S. Cl. .................... 530/358; 514/2
(58) Field of Search .................... 530/350, 352, 530/358, 324, 828; 514/2

(56) References Cited

U.S. PATENT DOCUMENTS

| | | | | |
|---|---|---|---|---|
| 4,925,677 A | * | 5/1990 | Feijen | 424/423 |
| 5,700,657 A | | 12/1997 | Beaudry et al. | 435/69 |
| 5,702,908 A | | 12/1997 | Picksley et al. | 435/7.8 |
| 5,756,455 A | * | 5/1998 | Kinzler et al. | 514/12 |
| 5,858,976 A | | 1/1999 | Burrell et al. | 514/12 |
| 5,955,263 A | | 9/1999 | Vogelstein et al. | 435/6 |
| 6,326,464 B1 | * | 12/2001 | Conseiller et al. | 530/324 |

FOREIGN PATENT DOCUMENTS

WO  WO9704092 A1 * 6/1997

OTHER PUBLICATIONS

Berg et al (Mar. 5, 1999, Cancer Research 59, 1180–1183).*
Kastin, AJ, 2001, Life Science, 69(11).*
Frost, SJ, 1993, J Cell Biochem, 52(2): 227–36.*
Selbo et al (2002, Tumour Biol 23, 103–12, abstract only).*
Medcalf et al (1993, Oncogene 8, 2847–2851 abstract only).*
Gardiol et al (Aug. 1998, Journal of General Virology 79, 1963–1970).*
Pocket Medical Dictionary at p. 422.*
Barak et al., "mdm2 Expression is induced by wild type p53 activity," 1993, EMBO J. 12:461–468.
Bondas et al., "Targeting of novel immunoliposomes prepared by a new antibody conjufation technique," 1999, International J. of Pharmaceutics 181:79–93.
Fletcher, "Drug delivery: strategies and technologies", Pharmaceutical Science and technology Today, 1998, 1:2:49–51.
GENBANK Accession No. M14694.

(List continued on next page.)

Primary Examiner—Larry R. Helms
Assistant Examiner—Misook Yu
(74) Attorney, Agent, or Firm—Ingrid A Beattle, Jr.; Mintz Levin Cohn Ferris Glovsky and Popeo PC (57) ABSTRACT

The invention provides compositions and methods for inhibiting degradation of p53, thereby enhancing p53-mediated tumor suppressor activity.

7 Claims, 4 Drawing Sheets

OTHER PUBLICATIONS

GENBANK Accession No. Y11416.

Gu et al., "use of hammerhead ribozyme with cationic liposomes to reduce leukocyte type 12–lipoxygenase expression in vascular smooth muscle," 1997, Mol. Cell. Biochem. 172:47–57.

Haupt et al., "Mdm2 promotes the rapid degradation of p53," Nature, 1997, 387:296–299.

He et al., "Inhibition of human squamous cell carcinoma growth in vivo by epideral growth factor receptor antisense RNA transcribed from the U6 promoter," J./ Natl. Cancer. Inst., Jul. 1998 15;90(14):1080–7.

Higgens et al., "Fast andsensitive multiple sequence alignments on a microcomputer," 1989, CABIOS 5(2):151–153.

Kay et al., "From peptides to drugs via phage display", Drug Discovery Today, 1998, 3:8:370–378.

Koning et al., "Selective transfer of a lipophilic prodrug of 5–florodeoxyuridine from immunoliposomes to colon cancer cells," 1999, Biochemica et Biophysica Acta 1420:153–167.

Livingstone, "Peptide and protein drug delivery and the academic–industry interface", Pharmaceutical Science and Technology Today, 1998, 1:8:324–325.

Madrid, Lee V., "Targeting p53", The Scientist, 13(4):14, Feb. 15, 1999.

Qing–Rong Chen and A. James Mixson, "Systematic Gene Therapy With P53 Inhibits Breast Cancer: Recent Advances And Therapeutic Implications", Fronteirs in Bioscience 3, Sep. 15, 1998. pp. 997–1004.

Scheffner et al., "The HPV–16 E6 and E6–AP complex functions as a ubiquitin–protein ligase in the ubiquitian of p53," Cell, 1993, Nov. 5;75(3):495–505.

Scheffner, Martin, "Ubiquitin, E6–AP, and Their Role in p53 Inactivation," Pharmacol. Ther., 1998, 78(3):129–139.

Smaglik, Paul, "Taking Aim at p53: Researchers are targeting the tumor suppressor with vectors, viruses, and small molecules," The Scientist, 13(2):6, Jan. 18, 1999.

Tana et al., "Antitumor Effect of Diptheria Toxin A–Chain Gene–containing Cationic Liposomes Conjugated with Monoclonal Antibody Directed to Tumor–Associated Antigen of Bovine Leukemia Cells," 1998, Journal J. of Cancer Res., 89:1201–1211.

Torchilin et al., "Targeted accumulation of polyethylene glycol–coated immunoliposomes in infarcated rabbit myocardium," 1992, FASEB J. 6:2716–2719.

Trivedi et al., "Liposome–Mediated Gene Transfer into Normal and Dystrophin–Deficient Mouse Myoblasts," 1995, J. Neurochem. 64:2230–2238.

Tseng et al., "Liposome–based gee therapy", Pharmaceutical Science and Technology Today, 1998, 1:5:206–213.

Vinyals A, Peinado MA, Gonzalea–Garrigues M, et al., "Failure of Wild–Type p53 Gene Therapy in Human Cancer Cells Expressing a Mutant p53 Protein." Gene Therapy 6(1):22–23, 1999.

Wang et al., "Antisense targeting of basic firoblast growth factor and fibroblast growth factor receptor–1 in human melanomas blocks intratumoral angiogenesis and tumor growth," 1997, Nat. Med. 3:887–893.

Yu et al., "Liposome–mediated in vivo E1A transfer suppressed dissemination of ovarian cancer cells that overexpress HER–2/neu," 1995, Oncogene 11:1383–1388.

* cited by examiner

INHIBITION OF P53 DEGRADATION

RELATED APPLICATION

This application claims the benefit from provisional application Serial No. 60/169,816, which was filed on Dec. 8, 1999.

STATEMENT AS TO FEDERALLY SPONSORED RESEARCH

This invention was funded in part by the U.S. Government under Grant Number R29CA76275 awarded by the National Institutes of Health. The Government has certain rights in the invention.

BACKGROUND OF THE INVENTION

The invention relates to tumor suppression.

The p53 tumor suppressor gene encodes a nuclear phosphoprotein with cancer-inhibiting properties. The development of human cancer may involve inactivation of this suppressor function through various mechanisms, including gene deletions and point mutations. The p53 protein is a multi-functional transcription factor involved in the control of cell cycle progression, DNA integrity and survival of cells exposed to DNA-damaging agents. Loss of p53 activity predisposes cells exposed to the acquisition of oncogenic mutations.

P53 is critical in maintaining ordered proliferation, growth, and differentiation of normal cells. Mutation in this gene may be one of the most significant genetic changes leading to the transformation of cells from normalcy to malignancy.

SUMMARY OF THE INVENTION

The invention provides compositions and methods for inhibiting degradation of p53, thereby enhancing p53-mediated tumor suppressor activity. Accordingly, the invention provides a polypeptide which contains the amino acid sequence of residues 92–112 of human p53 (PLSSSVPSQKTYQGSYGFRLG; SEQ ID NO:1). The polypeptide is substantially pure and inhibit degradation of endogenous p53 in a mammalian cell. The invention includes a polypeptide with the amino acid sequence PLSSSVPSQ KTYQGSYGFXLG (SEQ ID NO:2; where "X" is a positively-charged amino acid. For example, "X" is lysine (L) or histidine (H). p53-derived inhibitory polypeptides include a polypeptide which contains residues 1–113. of SEQ ID NO:3; a polypeptide which contains the proline-rich domain (PRD; residues 45–113 of SEQ ID NO:3) of p53; a polypeptide which does not contain the N-terminal acidic transactivation domain (TAD; residues 1–44 of SEQ ID NO:3 of p53; a polypeptide which does not contain a DNA binding domain (DBD; amino acids 144–290 of p53; a polypeptide which does not contain the oligomerization domain (OD; amino acids 319–363 of p53, and a polypeptide which does not contain residues 1–42 of SEQ ID NO:3.

The polypeptide is preferably at least 20 residues, more preferably at least 25 residues, more preferably at least 30 residues, more preferably at least 40 residues, and most preferably at least 50 residues in length. The polypeptide is less than the full-length of a naturally-occurring p53 polypeptide, i.e. the polypeptide is less than 393 amino acids in length.

The invention also includes peptide mimetics of p53 polypeptides. For example, the peptide mimetic contains the amino acid sequence of SEQ ID NO:1 or 2.

A method of inhibiting p53 degradation in a cell, e.g., a tumor cell or precancerous cell, is carried out by contacting the cell with a p53-derived inhibitory polypeptide described above. For example, the polypeptide contains the amino acid sequence of SEQ ID NO:1 or 2. Any cancer characterized by a p53 mutation or aberrant p53 expression is treated by the methods of the invention, e.g., squamous cell carcinoma, ovarian cancer, lung cancer (non-small cell and small cell carcinoma), pancreatic cancer, leukemias such as acute lymphoblastic leukemia, lymphomas, gliomas, and neuroblastomas. Cancers characterized by aberrant Mdm2 expression, e.g., overexpression or amplification, are also treated. Such cancers include sarcomas such as osteosarcoma as well as colon carcinoma, melanoma, choriocarcinoma, breast carcinoma, glioblastoma, neuroblastoma, and rhadomyosarcoma.

The methods are also useful to treat cancers in which p53 is degraded by human papillomavirus (HPV) E6 protein. For example, cervical cancers, in which HPV is often an etiological factor, are treated by administering a p53 inhibitory peptide to reduce E6-mediated degradation of endogeneous cellular p53.

In addition to administering p53-derived inhibitory polypeptides, DNA encoding such polypeptides are administered. For example, an isolated DNA encoding a polypeptide which contains the amino acid sequence of SEQ ID NO:1 or 2 is delivered to a target cell in a manner that allows uptake of the DNA by the cell and intracellular expression of the recombinant polypeptide in the cell.

Also within the invention is a degradation-resistant p53 polypeptide. A degradation-resistant polypeptide is refractory to Mdm2 or E6-mediated degradation but retains a tumor suppressor activity of p53, e.g., transcriptional activity or induction of apoptotic death of a cancer cell. For example, a degradation-resistant p53 mutant has a mutation in a degradation signal sequence of p53 such as a deletion (e.g., lacking the amino acid sequence of SEQ ID NO:1) or a point mutation (e.g., the amino acid at position 110 of p53 is substituted with an amino acid that is not positively charged). Preferably, the mutant contains an N-terminal transcriptional transactivation domain, e.g., amino acids 1–42 of SEQ ID NO:3 or amino acids 1–44 of SEQ ID NO:3. More preferably, the degradation-resistant p53 mutant retains at least 50%, more preferably at least 75%, more preferably 85%, more preferably 90%, more preferably 95%, more preferably 99%, and most preferably 100% of the tumor suppressive activity of a naturally-occurring p53 protein. Tumor suppressive activity is transcription activation, i.e., the ability to trans-activate transcription of a target gene such as Mdm2, or induction of apoptosis of tumor cells. A degradation-resistant p53 mutant polypeptide induces apoptosis in tumor cells.

The invention also includes an isolated DNA encoding a degradation-resistant p53 polypeptide and a method of inhibiting tumor growth by contacting a tumor cell with such a polypeptide or nucleic acid encoding it.

Other features and advantages of the invention will be apparent from the following description of the preferred embodiments thereof and from the claims.

DETAILED DESCRIPTION p53 encodes a protein that acts as a transcription factor and serves as a key regulator of the cell cycle. A p53 abnormality is associated with a variety of malignant tumors including brain cancers, soft-tissue sarcoma, breast cancer, adrenal tumors, bone cancer, cancer of the lung, prostate, pancreas, and colon as well as lymphoma and melanoma.

Damage to cellular DNA initiates increased expression of p53 which leads to arrest of the cell cycle. The interruption permits DNA repair to occur before the cell resumes the cell cycle and normal cell proliferation. If repair of the DNA is not successful, the cell then undergoes apoptotic cell death. When p53 mutates, DNA damaged cells are not arrested in G1 and DNA repair does not take place. The failure to arrest DNA-damaged cells is repeated in subsequent cell cycles permitting and contributes to tumor formation and cancer.

Mdm2 and E6 proteins inactivate p53 by promoting its degradation. Inhibition of Mdm2- and/or E6-mediated degradation results in an increase of p53 protein levels in the cell and restores or augments tumor suppressor function. A small peptide having an amino acid sequence corresponding to part or all of the degradation signal sequence of p53 efficiently blocks p53 degradation. For example, introduction of such a peptide into Mdm2-overexpressing or E6-positive cancer cells, e.g., by antibody-tagged liposome-mediated transfer, increases p53 protein levels in the neoplastic cells and leads to death of the cancer cells. The inhibitory peptide functions by blocking Mdm2 or E6 mediated degradation of p53. The cytotoxic effect is selective for cancer cells and does not affect normal cells.

Degradation Sequence

A sequence element from p53 which functions as a degradation signal for both oncogene Mdm2 and human HPV E6-mediated degradation of p53 was identified. A synthetic peptide with an amino acid sequence that corresponds to the degradation signal abrogates Mdm2 and E6-mediated degradation of p53.

TABLE 1

Human p53 amino acid sequence

| | | | | | | |
|---|---|---|---|---|---|---|
| MEEPQSDPSV | EPPLSQETFS | DLWKLLPENN | VLSPLPSQAM | DDLMLSPDDI | EQWFTEDPGP | 61 |
| DEAPRMPEAA | PRVAPAPATP | TPAAPAPAPS | WPLSSSVPSQ | KTYQGSYGFR | LGFLHSGTAK | 121 |
| SVTCTYSPAL | NKMFCQLAKT | CPVQLWVDST | PPPGTRVRAM | AIYKQSQHMT | EVVRRCPHHE | 181 |
| RCSDSDGLAP | PQHLIRVEGN | LRVEYLDDRN | TFRHSVVVPY | EPPEVGSDCT | TIHYNYMCNS | 241 |
| SCMGGMNRRP | ILTIITLEDS | SGNLLGRNSF | EVRVCACPGR | DRRTEEENLR | KKGEPHHELP | 301 |
| PGSTKRALPN | NTSSSPQPKK | KPLDGEYFTL | QIRGRERFEM | FRELNEALEL | KDAQAGKEPG | 361 |
| GSRAHSSHLK | SKKGQSTSRH | KKLMFKTEGP | DSD (SEQ ID NO:3; degradation signal sequence underlined) | | | |

TABLE 2 p53 nucleic acid sequence

```
accgtccagg gagcaggtag ctgctgggct ccggggacac tttgcgttcg ggctgggagc
gtgctttcca cgacggtgac acgcttccct ggattggcag ccagactgcc ttccgggtca
ctgccatgga ggagccgcag tcagatccta gcgtcgagcc ccctctgagt caggaaacat
tttcagacct atggaaacta cttcctgaaa acaacgttct gtccccttg ccgtcccaag
caatggatga tttgatgctg tccccggacg atattgaaca atggttcact gaagacccag
gtccagatga agctcccaga atgccagagg ctgctcccgc cgtggcccct gcaccagcga
ctcctacacc ggcggcccct gcaccagccc cctcctggcc cctgtcatct tctgtccctt
cccagaaaac ctaccagggc agctacggtt tcCGTctggg cttcttgcat tctgggacag
ccaagtctgt gacttgcacg tactcccctg ccctcaacaa gatgttttgc caactggcca
agacctgccc tgtgcagctg tgggttgatt ccacaccccc gcccggcacc cgcgtccgcg
```

TABLE 2-continued p53 nucleic acid sequence

```
ccatggccat ctacaagcag tcacagcaca tgacggaggt tgtgaggcgc tgcccccacc
atgagcgctg ctcagatagc gatggtctgg cccctcctca gcatcttatc cgagtggaag
gaaatttgcg tgtggagtat ttggatgaca gaaacacttt tcgacatagt gtggtggtgc
cctatgagcc gcctgaggtt ggctctgact gtaccaccat ccactacaac tacatgtgta
acagttcctg catgggcggc atgaaccgga ggcccatcct caccatcatc acactggaag
actccagtgg taatctactg ggacggaaca gctttgaggt gcgtgtttgt gcctgtcctg
ggagagaccg gcgcacagag gaagagaatc tccgcaagaa aggggagcct caccacgagc
tgccccagg gagcactaag cgagcactgc ccaacaacac cagctcctct ccccagccaa
agaagaaacc actggatgga gaatatttca cccttcagat ccgtgggcgt gagcgcttcg
agatgttccg agagctgaat gaggccttgg aactcaagga tgcccaggct gggaaggagc
caggggggag cagggctcac tccagccacc tgaagtccaa aaagggtcag tctacctccc
gccataaaaa actcatgttc aagacagaag ggcctgactc agactga (SEQ ID NO:8;
coding sequence begins at initiating "atg" codon indicated
by underline; nucleotide sequence encoding degradation signal
(amino acids 92-110 of p53) is underlined; codon which encodes
amino acid 110 is indicated by uppercase letters).
```

TABLE 3

Human p73 amino acid sequence

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGVKKRRHG DEDTYYLQVR
GRENFEILMK LKESLELMEL VPQPLVDSYR QQQQLLQRPS HLQPPSYGPV LSPMNKVHGG
MNKLPSVNQL VGQPPPHSSA ATPNLGPVGP GMLNNHGHAV PANGEMSSSH SAQSMVSGSH
CTPPPPYHAD PSLVSFLTGL GCPNCIEYFT SQGLQSIYHL QNLTIEDLGA LKIPEQYRMT
IWRGLQDLKQ GHDYSTAQQL LRSSNAATIS IGGSGELQRQ RVMEAVHFRV RHTITIPNRG
GPGGGPDEWA DFGFDLPDCK ARKQPIKEEF TEAEIH (SEQ ID NO:10)
```

Human p53 amino acid sequence and nucleic acid sequence encoding the protein is available from GENBANK™ (Accession no. M14694). Human p73 amino acid sequence and nucleic acid sequence encoding the protein is available from GENBANK™ (Accession no. Y11416).

The binding of Mdm2 to p53 is required for targeting p53 for degradation. p73, however, binds to Mdm2 but is refractory to Mdm2-mediated degradation, indicating that binding to Md2 is not sufficient for degradation. By utilizing the structural homology between p53 and p73, p53–p73 chimeras were generated to determine the additional sequence element of p53 involved in the regulation of its stability. Replacing amino acids 92–112 of p53 with the corresponding region of p73 results in a protein that is not degradable by Mdm2. Removal of the amino acid 92–112 of p53 by deletion also results in a non-Mdm2-degradable protein. This P53 fragment (amino acids 92–112) converts p73 from refractory into sensitive to Mdm2-mediated degradation. These data indicate amino acids 92–112 of p53 function as a degradation signal. Another protein may recognize the degradation signal and coordinate with Mdm2 to target p53 for degradation.

The following materials and methods were used to generate the data described herein.

Cell Culture and Transfections

All cells were maintained in MEM (GIBCO-BRL) containing 10% FBS (Sigma), 100 units/ml penicillin and 100 µg/ml streptomycin. Transfections were performed with a standard calcium phosphate method or with Lipofectamine (GIBCO-BRL). DNA was transfected into a number of different tumor cell types, e.g., embryonic kidney sarcoma such as 293T cells; human small cell lung cancer such as H1299 cells; human sarcoma cells such as U2OS and Saos-2 cells; and human breast cancer cells such as MCF-7 cells. Transcriptional activity, i.e., the ability to trans-activate a target gene, was measured according to standard methods, e.g., that described by Barak et al., 1993, EMBO J. 12:461–468. Transactivation of the the target gene luciferase was measured. Luciferase activities were assayed 24 hours post-transfection with an enhanced luciferase assay kit (1800K; Analytical Luminescence). Apoptosis is detected using a standard DNA fragmentation test.

Plasmids

The p53–p73 chimeras were prepared by a standard two-step PCR. The point-mutation mutants of p53, (R273H) or p73 (R293H), as well as the deletion mutants were also generated by PCR using standard methods. Restriction enzyme digestion and DNA sequencing confirmed the identity of each construct.

In vitro Protein-Binding Assay

Mdm2 and p73 were expressed as glutathione S-transferase (GST) fusion proteins bound to glutathione-Sepharose beads (Pharmcia) and incubated with either in vitro translated $^{35}$S-labeled protein or cell lysates. The adsorbates were washed and analyzed by SDS-PAGE followed by either autoradiography or immunoblotting to confirm the identity of the fusion protein.

Immunoprecipitation and Immunoblot Analysis

Immunoprecipitations were performed using methods known in the art. Cell lysates were prepared in 0.5% Triton X-100 lysis buffer (50 mM HEPES, pH 7.5, 150 mM NaCl, 1 mM EDTA, 1 mM EGTA, 1 mM sodium orthovanadate, 1 mM dithiothreitol, 1 mM NaF, 2 mM phenylmethysulfonyl fluoride, and 10 µg/ml each of leupeptin, and aprotinin) and incubated with anti-Flag agarose beads (M5, Sigma) for 8–12 hours. Immune complexes and whole lysates were separated by SDS-PAGE and then transferred to nitrocellulose filter. The filters were incubated with anti-p53 (Ab-6; Oncogene Science), anti-MDM2 (Ab-1; Oncogene Science), Anti-WAF1 (Ab-3: Oncogene Science), anti-GFP (Clontech) and anti-FLAG (M5, Sigma) antibodies. Proteins were detected with an ECL system (NEN).

Half-life Determination

For measuring half-life of the p53, p73 or p53-p73 chimeras, U2OS cells expressing the indicated cDNA were treated with cycloheximide (final concentration 40 μg/ml) and harvested. Cells were processed as described above for lysates and Western blotting.

EXAMPLE 1

Mdm2 Binds to p73 and Inhibits Its Transcriptional Activity but Fails to Target p73 for Degradation Mdm2 negatively regulates p53 activity by directly blocking p53's activity as a transcription factor and by targeting it for degradation. Studies were carried out to investigate whether Mdm2 regulates p73 and P53 in a similar manner. Since the binding of Mdm2 to p53 is necessary for its inhibitory activity, assays were carried out to determine whether Mdm2 also binds to p73. Vectors expressing Flag-tagged p73α or p73β were cotransfected with a pCMV-Mdm2 construct into 293T cells. Flag-tagged p53 and Rad52, an unrelated protein, were included as controls. Cell lysates were prepared from the transfectants 24 hours post-transfection and subjected to immunoprecipitation with an anti-Flag antibody. Western analysis with an anti-Mdm2 antibody exhibited that Mdm2 is readily detected in the p53, but not the Rad52 immunocomplex. Like p53, both p73α and p73β are also associated with Mdm2. To further investigate the nature of the Mdm2/p73 interaction, the N-terminus, middle region, and the C-terminus of p73 were expressed as GST-fusion proteins that were then tested for their ability to bind to in vitro translated Mdm2. In agreement with the N-terminal location of the Mdm2-binding motif, the GST-pull down assay demonstrated a specific interaction between Mdm2 and the p73 N-terminus but not with other regions.

Mdm2 binds to p73 and inhibits its transcriptional activity. Like p53, both isoforms of p73 associate with Mdm2 in vivo. 293T cells were cotransfected with vectors expressing Flag-p73α or Flag-p73β and pCMV-Mdm2. Flag-p53 and Flag-Rad52 were included as controls. After 24 hours, cell lysates prepared from the transfectants were subjected to immunoprecipitation with an anti-Flag antibody. The whole cell extracts (WCE) and immunoprecipitates were analyzed by immunoblotting with anti-Flag or anti-Mdm2. Like p53, the N-terminus of p73 interacts with Mdm2. $^{35}$S-labeled Mdm2 was incubated with GST-p73 fusion proteins or GST-p53 fusion proteins. The adsorbates (1/50 of the $^{35}$S-labeled Mdm2 was loaded as an input) were analyzed by SDS-PAGE and autoradiography.

Figure 1:
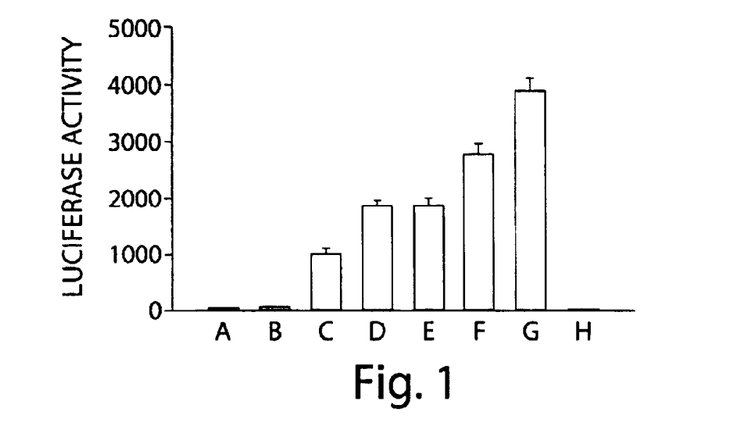
FIG. 1 is a bar graph showing that p73 transactivates Mdm2 promoter. Saos-2 cells were cotransfected with 0.5 μg of mdm2NA-Luc plasmid and: 5 μg pCDNA3-Flag control vector (bar A); 0, 2.5, or 5 μg of Flag-p73α (bars B, C, or D); or 2.5, or 5 μg of Flag-p73β_(bars E, or F); or 5 μg of Flag-p53 (bar G); or 0.5 μg of mdm2NA-Luc with a mutated p53 binding site and 5 μg of Flag-p53 (bar H). pCDNA3-Flag empty vector was used to control the DNA amounts. Luciferase activity was measured with a normalized protein concentration 24 hours post-transfection.
Figure 2:
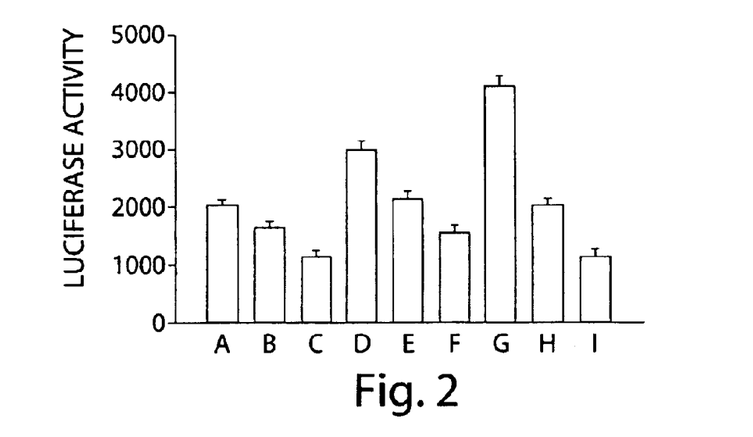
FIG. 2 is a bar graph showing that Mdm2 inhibits p73 transcriptional activity in a dose-dependent manner. Saos-2 cells were cotransfected with 0.5 μg of mdm2NA-Luc plasmid and; 5 μg of Flag-p73α with 0, 2.5, or 5 μg of pCMV-Mdm2 (bars A, B, or C); or 5 μg of Flag-p73β with 0, 2.5, or 5 μg of pCMV-Mdm2 (bars D, E, or F); or 5 μg of Flag-p53 with 0, 2.5, or 5 μg of pCMV-Mdm2 (bars G, H, or I). Luciferase assays were done 24 hours post-transfection.
Figure 3:
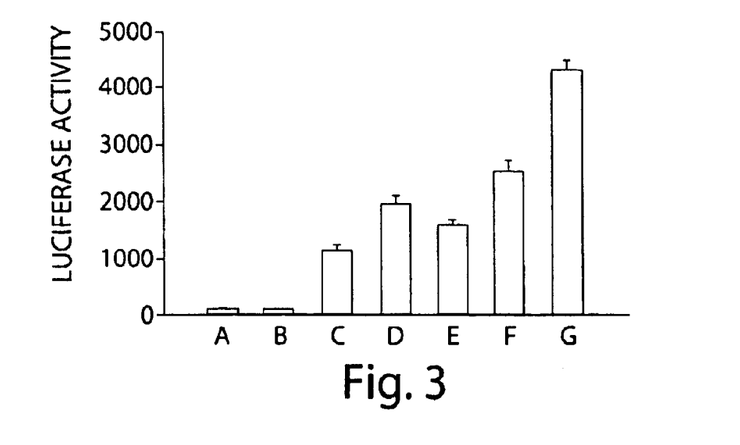
FIG. 3 is a bar graph showing that p73 transactivates p21 promoter. Similar luciferase assays were performed with 0.5 μg of p21-Luc plasmid and: 5 μg pCDNA3-Flag control vector (bar A); 0, 2.5, or 5 μg of Flag-p73α (bars B, C, or D); or 2.5, or 5 μg of Flag-p73β (bars E, or F); or 5 μg of Flag-p53 (bar G).

Like p53, p73 interacts with the N-terminus of Mdm2. Lysates from cells expressing Flag-p73β and Flag-p53 were incubated with the indicated GST-Mdm2 fusion proteins. The adsorbates were resolved by SDS-PAGE and immunoblotted with anti-p73 or anti-p53. The N-terminal of Mdm2 is responsible for its binding to p53. To determine whether p73 also binds to the same region of Mdm2, a series of truncated Mdm2 GST-fusion proteins were generated for incubation with cell lysates prepared from cells overexpressing p73 and p53. Immunoblotting analysis with an anti-p73 antibody revealed that p73, like p53, binds specifically to the full-length Mdm2 as well as to the N-terminus of Mdm2. The binding of Mdm2 to the N-terminus of p53 results in an inhibition of the p53 transactivation activity, likely by blocking the nearby transactivation domain. Having shown that Mdm2 binds to the transactivational domain of p73, studies were carried out to determine whether Mdm2 also inhibits the transcriptional activity of p73. The p73 transcriptional activity was assessed by a reporter construct containing the luciferase gene driven by a p53 enhancer from the Mdm2 promoter; the same site can be bound by p73. p73 stimulated the luciferase activity in a dose-dependent manner (FIG. 1). Little, if any, induction of luciferase activity was associated with a similar reporter driven by the Mdm2 promoter with a mutated p53-binding site (FIG. 1, bar H), demonstrating the specificity of this effect. Comparable results were also obtained using the p21 promoter (FIG. 2). To determine the effect of Mdm2, increasing amounts of Mdm2 expression vectors were transfected into Saos-2 cells with p73 and the luciferase activity was assayed 24 hours post-transfection. The results demonstrate that the transactivational activity of p73, as that of p53, is inhibited by the expression of Mdm2 in a dose-dependent manner (FIG. 3).

Mdm2 Does Not Promote Degradation of p73

In addition to blocking the p53 transcription activity, one of the key mechanisms for Mdm2-mediated regulation of p53 activity is to promote p53 degradation. Since the binding of p53 to Mdm2 is essential for Mdm2-mediated degradation and p73 binds to Mdm2, the ability of Mdm2 to promote p73 degradation was investigated. Coexpression of Mdm2 was associated with degradation of Flag-p53 but not Flag-p73. Saos-2 cells were cotransfected with 2.5 μg of Flag-p53, Flag-p73α or Flag-p73β with 5 μg of pCMV-Mdm2 or pCMV-empty vector. 0.5 μg of pEGFP-C1 plasmid was included as the transfection control. Cell lysates were prepared 24 hours after transfection and subjected to immunoblotting analysis with anti-Flag, anti-Mdm2 or anti-GFP.

Similar experiments were performed with pEGFP-p53; pEGFP-p73α or pEGFP-p73β and analyzed with anti-GFP or anti-Mdm2. Mdm2 is incapable of degrading p73 in MCF-7 and H1299 cells. MCF-7 or H1299 cells were cotransfected with 2.5 μg of Flag-p53, Flag-p73α or Flag-p73β with 5 μg of pCMV-Mdm2 or pCMV-empty vector. The cells were subjected to Western analysis with anti-Flag, anti-Mdm2 or anti-GFP.

Flag-tagged p73 was cotransfected with pCMV-Mdm2 or pCMV-empty vector into Saos-2 cells. Flag-tagged p53 was included as a positive control. Cell lysates were prepared from the transfectants 24 hours post-transfection and subjected to Western analysis. As expected, immunoblotting analysis with an anti-Flag antibody exhibited Mdm2-dependent ubiquitination as well as degradation of p53. Surprisingly, neither ubiquitination nor degradation of p73 was detected when Mdm2 was coexpressed. To confirm this finding, Mdm2-mediated degradation was assessed with a different set of expression constructs. GFP-tagged p53, 73α, or p73β expression vectors were prepared and expressed with or without coexpression of Mdm2. p53, but not p73, was degraded by the coexpression of Mdm2. To determine whether the resistance of p73 to Mdm2-mediated degradation is cell type specific, similar experiments were carried out with MCF-7 cells as well as with H1299 cells. The results showed that no apparent Mdm2-mediated degradation of p73 was detected in either of the cell lines. Together these results indicate that like p53, Mdm2 associates with p73 and inhibits its transcriptional activity, but in contrast to p53, Mdm2 does not target p73 for degradation.

Preparation of the Chimeras of p53–p73

The observation that despite binding to Mdm2, p73 is refractory to Mdm2-mediated degradation indicates that the binding of Mdm2 to p53 is not sufficient for degradation and an additional element is required. A series of p53–p73 chimeras were generated and then tested for their sensitivity to Mdm2-mediated degradation. The high degree of structural homology between p53 and p73 permitted switching each of the p53 domains with the corresponding region of p73 without disturbing their conformation.

Figure 5:
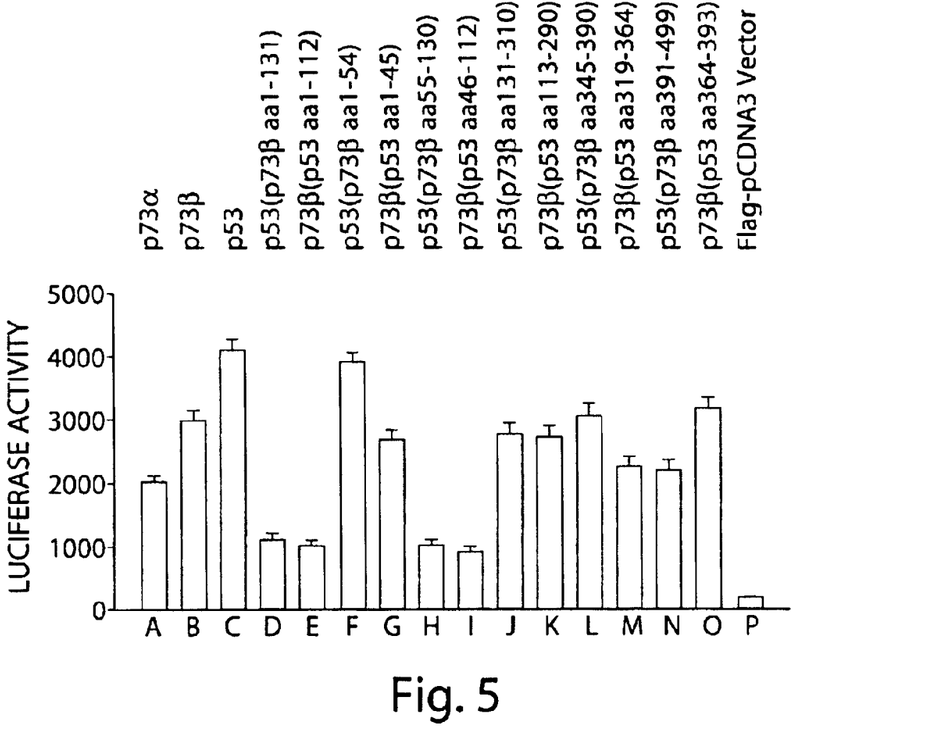
FIG. 5 is a bar graph showing that p53–p73 chimeras retain transcriptional activity.

The p53–p73 chimeras retained transcriptional activity. The p53–p73 chimeras were prepared by switching each segment between p53 and p73 at the indicated position with using standard two-step PCR. Saos-2 cells were cotransfected with 2.5 $\mu$g of indicated expression vectors and 0.5 $\mu$g of pEGFP-C1 plasmid was included as the transfection control. Cell lysates were prepared 24 hours after transfection and subjected to immunoblotting analysis with anti-p21, anti-Flag or anti-GFP. Saos-2 cells were cotransfected with 0.5 $\mu$g of p21-Luc plasmid and 2.5 $\mu$g of construct. pCDNA3-Flag empty vector was used to control the DNA amounts. Luciferase activity was measured with a normalized protein concentration 24 hours post-transfection (FIG. 5).

Restriction enzyme digestion and DNA sequencing confirmed the identity of each chimera. To test whether the chimeras retained wild-type function, Flag-pCDNA3 vectors expressing the chimera were prepared and then tested for their ability to induce p21 expression. Each of the vectors was transfected transiently into Saos-2 cells, which lack both p53 and p73, and the cells were analyzed for induction of p21 by Western blot 24 hours post-transfection. The levels of p21 were induced, though to variable extents, by the expression of the chimeras, indicating their transactivational competence. Immunoblotting with an anti-Flag antibody showed comparable levels of expression achieved for the wild-type proteins and chimeras. Consistent with the results from the Western analysis, transcriptional activity assessed by the luciferase reporter gene with the p21 promoter demonstrated that the chimeras were transcriptionally active (FIG. 5).

OD of p53 is Dispensable for Mdm2-mediated Degradation

The role of p53's OD in Mdm2-targeted degradation has been disputed. To address this issue, the OD-swapping chimeras were subjected to analysis of their sensitivity to Mdm2-targeted degradation.

PCDNA-Flag vectors containing p73$\beta$, p53 or the indicated chimeras were coexpressed with GFP-p53 or GFP-p73, respectively. Anti-Flag immunoprecipitations were performed with cell lysates prepared from the transfectants 24 hours post-transfection. The WCE and anti-Flag immunocomplexes were analyzed by Western blotting with anti-GFP, or anti-Flag. Switching the OD between p53 and p73 does not alter their sensitivity to Mdm2-mediated degradation. 2.5 $\mu$g of the indicated vectors was cotransfected with or without 5 $\mu$g of pCMV-Mdm2 into Saos-2 cells. 0.5 $\mu$g of pEGFP-C1 plasmid was included as the transfection control. Cell lysates were prepared 24 hours after transfection and subjected to immunoblotting analysis with anti-Flag, or anti-GFP.

To determine whether the domain-swapping has an impact on oligomerization, the capability of the chimeras to form oligomers in vivo was assessed by examining protein-protein interaction using an IP-Western analysis. Flag-tagged p73, p53 or the p53–p73 chimeras with switched ODs were coexpressed with GFP-tagged p53. Lysates were prepared from the transfectants 24 hours post-transfection and subjected to immunoprecipitation with an anti-Flag antibody. Anti-GFP immunoblotting analysis demonstrated that GFP-p53 only associates with Flag-p53 but not Flag-p73. This observation indicated that p53 forms homo-oligomers but not hetero-oligomers in vivo. Switching the OD between p53 and p73 results in the hetero-complex formation. p53 is readily detected in the immune complexes of p73$\beta$(p53aa319–364) that contains the OD of p53, indicating that it is the sequence of OD that determines the specificity of oligomerization. Similar results were observed in a parallel experiment where Flag-tagged p73, p53 or the chimeras were coexpressed with GFP-p73. Anti-GFP immunoblotting analysis revealed that GFP-p73 only associates with Flag-p73 and with the chimera containing the OD of p73 but not with Flag-p53 or the p73 chimera with OD of p53. Taken together, the results indicate that the OD swapping chimeras are functional in oligomer formation. Furthermore, the results demonstrated that both p53 and p73 can only form homo-oligomers.

If the OD of p53 was essential for Mdm2-mediated degradation, an alteration of sensitivity to degradation by Mdm2 should result from switching the OD between p53 and p73. To test this, each of the OD swapping chimeras was transfected into Saos-2 cells with or without Mdm2; the protein levels were determined by immunoblotting with an anti-Flag antibody 24 hours post-transfection. Wild-type p53 and p73 were included as controls. As expected, p53, but not p73, was degraded by the coexpression of Mdm2. Switching the OD between p53 and p73 resulted in no apparent sensitivity change to Mdm2-mediated degradation. The p53 (p73$\beta$aa345–390) remained sensitive and the p73$\beta$ (p53aa319–364) was still refractory to Mdm2-targeted degradation. The result indicated that the OD of p53 contributes little, if any, to the sensitivity of Mdm2-mediated degradation.

Role of the N-terminus of p53 in Mdm2-mediated Degradation

The structural determinant of p53 for Mdm2-mediated degradation was identified. The N-terminal 131 amino acids of p53 are necessary and sufficient for Mdm2-mediated degradation. 2.5 $\mu$g of the indicated vectors was cotransfected with or without 5 $\mu$g of pCMV-Mdm2 into Saos-2 cells and the cells were analyzed as described above. Levels of the proteins expressed were determined by Western analysis with anti-Flag. Anti-GFP immunoblotting demonstrated that comparable transfection efficiency was achieved.

Figure 4:
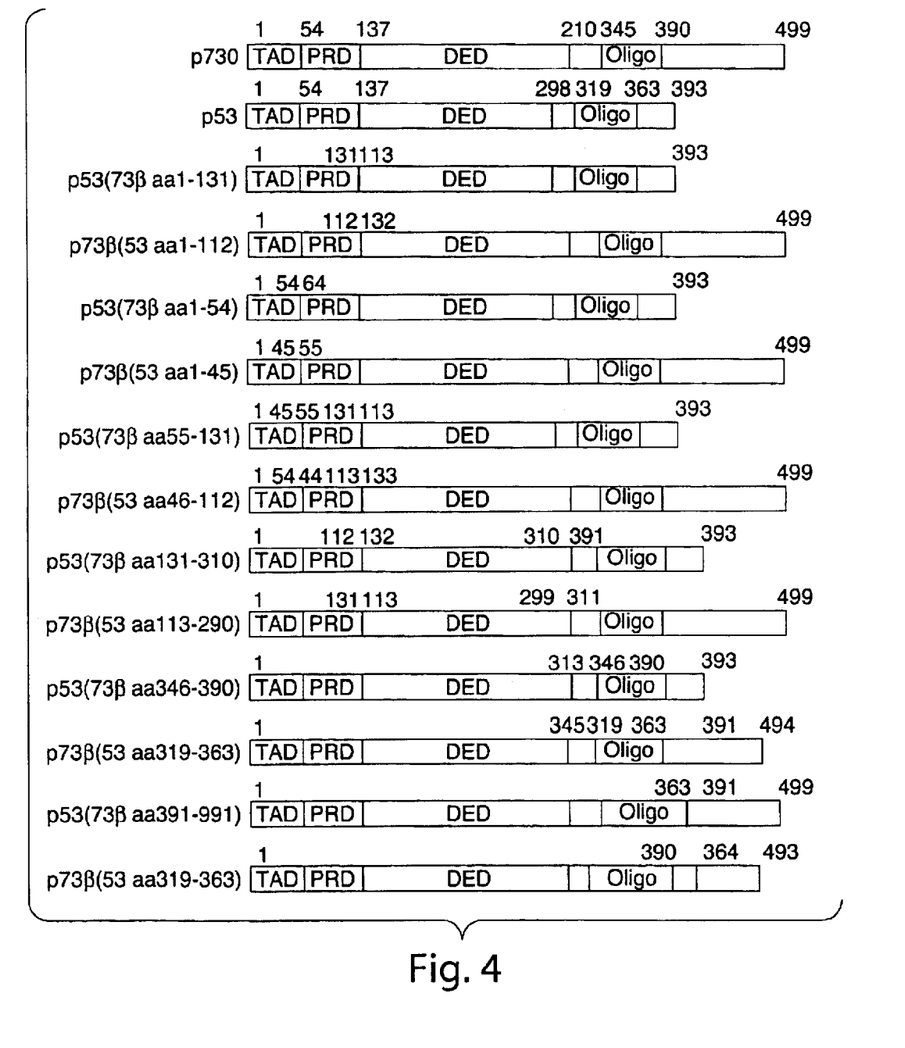
FIG. 4 is a diagram of p53–p73 chimeras showing the domain structure of each construct.

The proline-rich domain but not the TAD of p53 is required for Mdm2-mediated degradation. The p53–p73 chimeras were analyzed as described above. Levels of the chimeras and transfection efficiency were determined by Western analysis with anti-Flag and anti-GFP. The p53–p73 chimeras with a more refined swapping at the proline-rich domain were prepared as shown in FIG. 4 by switching each segment between p53 and p73 at the indicated position.

p21 levels were induced by the expression of the chimeras. A vector (2.5 $\mu$g) containing the indicated cDNA was transfected into Saos-2 cells and the transfectants were analyzed by Western blotting with anti-p21 and anti-Flag 24 hours post-transfection. The segment spanning amino acids 92–112 of p53 was essential for Mdm2-mediated degradation. The p53–p73 chimeras with more refined swapping at the proline-rich domain were tested for sensitivity to Mdm2-mediated degradation as described above. Levels of the chimeras and transfection efficiency were determined by Western analysis with anti-Flag and anti-GF. The p53–p73 chimeras bound to Mdm2 with an affinity comparable to their wild-type counterpart. Flag-tagged vectors expressing wild-type p53, p73 or the indicated chimeras were coexpressed with pCMV-Mdm2. Cell lysates were prepared 24 hours post-transfection and subjected to anti-Flag immunoprecipitation. The immunocomplexes were resolved by SDS-PAGE, transferred onto nitrocellulose membrane and analyzed by immunoblotting with anti-Mdm2 and anti-Flag. The p53 mutant lacking amino acids 92–112 was no longer sensitive to Mdm2-mediated degradation.

The p53 (del.aa92–112) mutant was tested for its sensitivity to Mdm2-mediated degradation. The corresponding deletion mutant of p73 was included as a control. Levels of the proteins and transfection efficiency were determined by Western analysis with anti-Flag and anti-GFP. The p53 or p73 deletion mutants retained their capability of binding to Mdm2. Association of the deletion mutants with Mdm2 was also examined.

The Mdm2-binding motif of p53 is located at its N-terminus and is conserved in p73. The finding that p73 binds to Mdm2 but is refractory to Mdm2-mediated degradation suggests that in addition to binding to Mdm2, another element(s) may be required for Mdm2-targeted degradation. A small domain of p53 at the N-terminus plays a role in its degradation by Mdm2. Except for the Mdm2-binding motif, the homology between p53 and p73 at the N-terminus is much less pronounced (25% identity), providing a potential structural basis for their distinct response to Mdm2-targeted degradation. The sensitivity of the chimeras p53 (p73βaa1–131) and corresponding p73(p53aa1–112) to Mdm2-mediated degradation was evaluated. The result demonstrated that switching the N-terminus between p53 and p73 is associated with a loss of sensitivity in p53 and gain of sensitivity in p73 to Mdm2-mediated degradation. These data indicate that the N-terminus of p53, consisting of amino acid 1–112, is indeed sufficient for Mdm2-targeted degradation. The p73β(p53aa1–112) becomes and the p53 (p73βaa1–131) remains capable of ubiquitination, which suggests that both the N- and C-terminus of p53 are involved in the ubiquitination. The finding that p53(p73βaa1–131) remains ubiquitinated but is resistant to degradation by Mdm2 indicates that ubiquitination and degradation are separable events.

The p53(1–131) region can be further divided into the TAD and the proline-rich region to evaluate the role of the TAD domain, the sensitivity of p53(p73βaa1–54) and p73β (p53aa1–45) to Mdm2-targeted degradation was measured surprisingly, the results demonstrated that the TAD of p53 is dispensable for Mdm2-mediated degradation, the p53 (p73βaa1–54) remains sensitive to and the p73β (p53aa1–45) is still refractory to Mdm2-mediated degradation. However, switching the proline-rich domain between p53 and p73, which results in chimeras of p53 (p73βaa55–131) and p73β(p53(aa46–112) respectively, converts p53 into being refractory and p73 into being sensitive to Mdm2-mediated degradation. Together, these results indicate that the proline-rich region but not the TAD of p53 is essential for its sensitivity to Mdm2-mediated degradation.

In an effort to map the minimum sequence required for Mdm2-mediated degradation, a more refined swapping at the proline-rich region was carried out to generate the p53–p73 chimeras. Flag-tagged vectors expressing the chimeras were prepared for testing their sensitivity to Mdm2-targeted degradation. The affect this refined domain swapping on the transcriptional activity was evaluated. Each of the vectors was transfected transiently into Saos-2 cells, and the cells were analyzed for induction of p21 by immunoblotting with an anti-p21 antibody, 24 hours post-transfection. The result demonstrated that chimeras are transcriptionally active as shown by the induction of p21 levels. Anti-Flag immunoblotting ensured comparable levels of wild-type and chimeras proteins expressed. To assess the response to Mdm2-mediated degradation, a vector containing the chimera cDNA was transfected into SaoS-2 cells with or without coexpression of Mdm2. The data showed that the amino acid 92–112 of p53 is required for Mdm2-mediated degradation as demonstrated by the observation that switching p53's (92–112) with the corresponding region of p73 (105–131) confers p73 with sensitivity and p53 with resistance to Mdm2-mediated degradation. In contrast, substitution of p53's 46–63 or 64–91 with the corresponding p73's 55–75 or 76–104, respectively, does not lead to any apparent alteration of their response to Mdm2-mediated degradation To rule out that the refractory nature of p53 (p73βaa105–131) to Mdm2-mediated degradation was due to an impaired binding to Mdm2, interaction between the chimera with Mdm2 was examined by IP-Western analysis. p53(p73βaa105–131) binds to Mdm2 with an affinity comparable to that of wild-type p53 and so does p73β (p53aa92–112), indicating no apparent effect on the Mdm2-binding from the swapping fusion. To further determine whether the gain of resistance in p53 and loss of resistance in p73 was due to an inhibitory effect of the amino acid 105–131 of p73 on degradation, a p53 deletion mutant lacking amino acid 92–112 and a corresponding mutant of p73 lacking amino acid 106–131 were made to test their sensitivity to Mdm2-mediated degradation. The result shows that removal of the amino acid 92–112 of p53 is associated with a lose of sensitivity to Mdm2-mediated degradation. Deletion of the corresponding region of p73, however, exhibited no apparent effect on its resistance to Mdm2-mediated degradation. IP-Western analysis demonstrated that the deletion mutants remained able to bind to Mdm2, indicating that loss of sensitivity of the p53 deletion mutant is not due to any defect in Mdm2-binding. Taken together, the results demonstrate that in addition to the N-terminus Mdm2-binding sequence, the 21 amino acid residues (92–112) of p53 is the sequence element of p53 that functions as the degradation signal for Mdm2-mediated degradation.

Role of the C-terminus and DBD of p53 in Mdm2-mediated Degradation

Contribution of the C-terminus and BDB of p53 to Mdm2-mediated degradation was evaluated as follows. The p53–p73 chimeras with their C-terminus switched were tested for sensitivity to Mdm2-mediated degradation. Levels of the chimeras and transfection efficiency were determined by Western analysis with anti-Flag and anti-GFP. The p53–p73 chimeras with their DBD switched were tested for their sensitivity to Mdm2-mediated degradation.

In an unstressed cell, the p53 protein is not only at a very low level but also in an inactive state. The extreme C-terminal region of p53 may prevent DNA binding through an allosteric mechanism. To study the role of p53's C-terminus and DBD in p53 degradation, the Mdm2-mediated degradation was measured using the chimeras in which the corresponding region of p73 was replaced the C-terminus of p53. The results showed that p53 (p73βaa310–495) became less sensitive to Mdm2-mediated degradation than wild-type p53, but p73β(p53aa291–393) did not gain any sensitivity, indicating that the C-terminus of p53 regulates its stability but is not the determinant for its sensitivity to Mdm2-mediated degradation. The DBD of p53 did not contribute to Mdm2-mediated degradation, as evidenced by the observation that there was no apparent change of sensitivity to the degradation by Mdm2 resulting from switching the DBDs between p53 and p73.

p53(p73βaa105–131) Has a Prolonged and p73β (p53aa92–113) Has a Shortened Half-life Studies were carried out to evaluate a correlation between Mdm2-mediated degradation and protein stability. A point mutation (R273H for p53 or R293H for p73) was introduced using known methods. Restriction enzyme digestion and DNA sequencing confirmed the mutation. 2.5 μg of the indicated expression vectors were transfected with 0.5 μg of pEGFPC1 plasmid into Saos-2 cells, and cell lysates from the transfectants were analyzed by immunoblotting with anti-Flag and anti-GFP 24 hours post-transfection.

Figure 6:
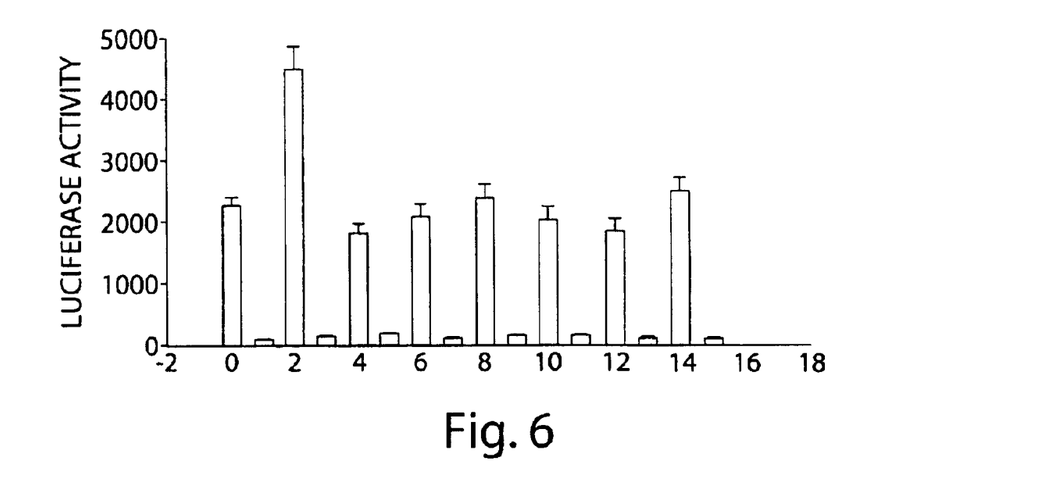
FIG. 6 is a bar graph showing that p53 mutants were transcriptionally inactive. p21-Luc was cotransfected with the vector into Saos-2 cells, and luciferase activity was measured 24 hours post-transfection. Results are mean ±SD from two experiments performed in triplicate.

Having identified the amino acid 92–112 of p53 as the degradation signal to Mdm2-mediated degradation, experiments were carried out to determine whether the changed sensitivity to Mdm2-mediated degradation corresponded to an altered stability by measuring the half-lives of the proteins. The capability of p53 and p73 to induce growth arrest and apoptosis impedes the expression of the wild-type proteins. To overcome this, p53 and p73 mutants were generated by introducing a point mutation into the DNA-binding domain (Arg273-His for p53 or corresponding Arg292-His for p73, as described above), that has been shown to result in an abrogation of DNA binding and transcriptional activity. When transiently transfected into Saos-2 cells, the mutants were expressed at levels comparable to, or even slightly higher than, their wild-type counterpart, but they were transcriptionally inactive as shown by the luciferase reporter assay with the p21 promoter (FIG. 6).

Figure 7A:
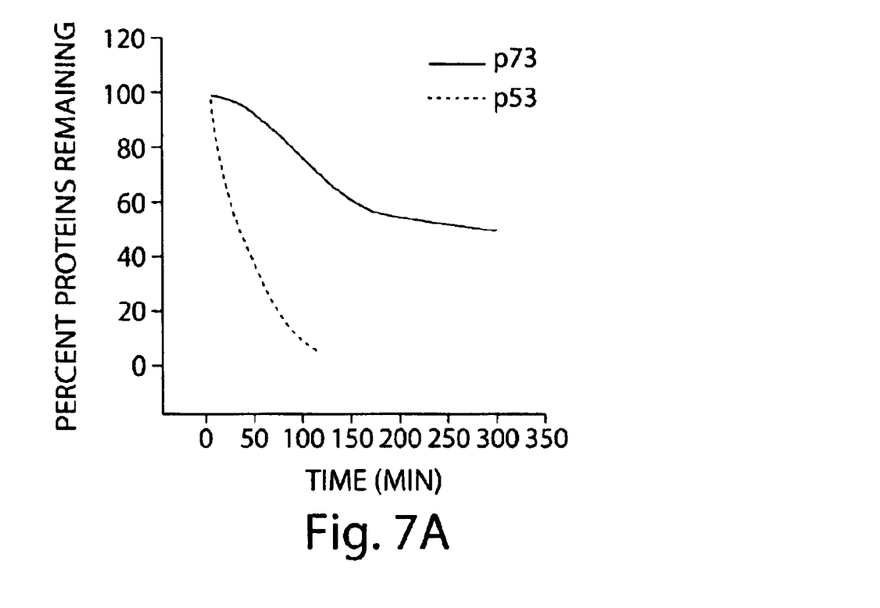
FIGS. 7A–B are a line graphs showing that amino acids 92–112 of p53 are critical for protein stability. U2OS cells were transfected with 2.5 μg of the indicated vector. The cells were treated with cyclohexamide (40 μg/ml) at 24 hours post-transfection and then harvested at 0, 30, 60, 120, 180 or 300 min afterward. Lysates from the cells were analyzed by anti-Flag Western blotting. Quantitation of the protein as a percentage of the starting levels was derived from a densitometric measurement of the Western blot signals.
Figure 7B:
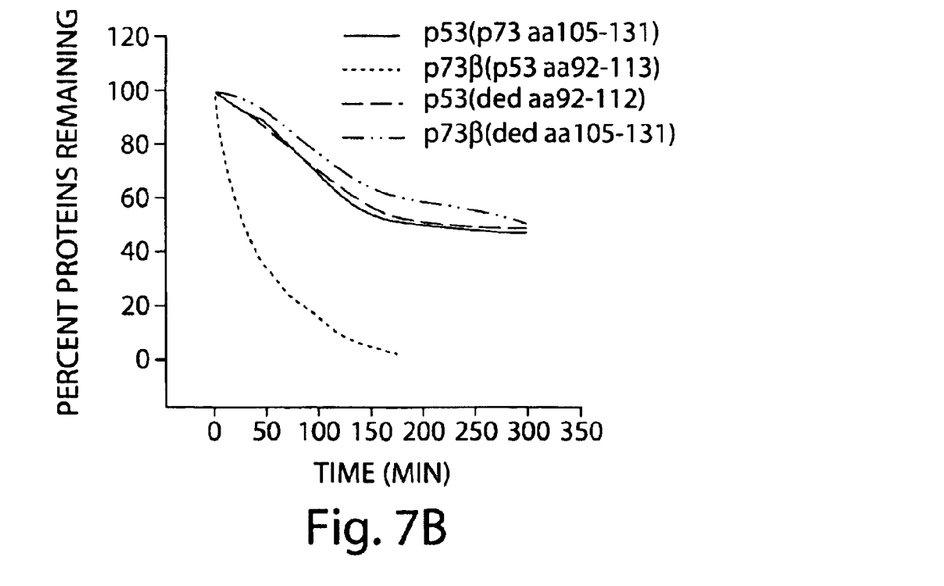

The half-life of the protein was determined by Western blot analysis in cells treated with the drug cyclohexamide, which inhibits de novo protein synthesis. The U2OS cells expressing the mutated p53 or p73 gene products were analyzed at 0, 30, 60, 120, 180 and 300 min. following addition of cyclohexamide. The results demonstrated that replacing the amino acid 92–112 of p53 with the corresponding region (105–131) of p73 results in a markedly prolonged half-life (FIGS. 7A–B). On the other hand, p73β (p53aa92–112) exhibited a much-shortened half-life in comparison to wild-type p73β. A significantly prolonged half-life is also evident in the p53 deletion mutant lacking the amino acid 92–112. Together the results demonstrate that the amino acid 93–112 of p53 is critical for control of p53 stability.

Regulation of p53 Degradation

Protein degradation of p53 is determined by a degradation signal in the sequence/structure of the protein. Other proteins may participate in the recognition of the degradation signal. While interaction with Mdm2 is required for targeting p53 for degradation, the observation that p73 binds to Mdm2 but is resistant to degradation by Mdm2 indicated the existence of an additional structural element unique to p53 needed for the recognition. Using the p53–p73 chimeras generated by switching each of p53's domains with the corresponding region of p73, a domain spanning amino acids 92–112 of p53 was identified as the element that functions as a degradation signal for Mdm2-mediated degradation. Replacement of the sequence (92–112) of p53 with the corresponding region of p73 was associated with a loss of its response to Mdm2-mediated degradation even though the chimera retained its capability of binding to Mdm2. Removal of the amino acid 92–112 domain of p53 by deletion also resulted in a loss of response to Mdm2-mediated degradation, indicating that in addition to the Mdm2-binding domain, amino acids 92–112 are required for degradation of p53 by Mdm2. The observation that amino acids 92–112 of p53 functions as a degradation signal for the Mdm2-mediated pathway is further supported by the finding that p73 gains sensitivity to Mdm2-mediated degradation once the 92–112 domain of p53 is fused into the corresponding region of p73. No apparent sequence homologue of the degradation signal sequence was identified in any known protein based on the Blast sequence homology search, indicating its uniqueness to p53.

Contrary to earlier studies, the OD of p53 was found to be dispensable for Mdm2-mediated degradation. The observation that p73β can oligomerize at levels comparable to p53 but is not degraded by Mdm2 supports data indicating that the OD of p53 is not essential for Mdm2-mediated degradation.

Contribution of the extreme C-terminus of p53 to its stability is reflected by a reduced sensitivity of the C-terminal chimera to Mdm2-mediated degradation. There is no significant homology between the C-terminal domain of p53 and p73 and its role remains unclear.

EXAMPLE 2

Degradation-resistant p53 Mutants

A p53 mutant with point mutation at position 110 was generated. An arginine was replaced with an alanine, changing a positively charged amino acid to one that is not positively-charged. This mutation renders the mutant polypeptide degradation-resistant. The mutant retains tumor suppressor activity, i.e., it is transcriptionally active and induces apoptotic death of tumor cells. p53-dependent apoptotic activity is dependent on the integrity of amino acids 46–90 of p53. p53 transcriptional activity requires the integrity of the TAD domain of p53. A degradation-resistant mutant of p53 is encoded by a sequence with contains a mutation in a region of the coding sequence of SEQ ID NO:8 which spans nucleotides 399–461, inclusive, but does not contain a mutation in nucleotides which encode the TAD domain and/or nucleotides which encode amino acids 46–90 of the wild type p53 amino acid sequence.

EXAMPLE 3

Inhibition of E6-mediated p53 Degradation

The p53 point mutants, deletion mutants, and p53/p73 chimeras described above were also tested for their ability to inhibit HPV E6-mediated degradation. A ubiquitin-dependent protein degradation assay, e.g., that described by Scheffner et al., 1993, Cell 75:495–505, was used. The data confirmed the observations described above in the Mdm2-dependent degradation studies. Replacement of amino acids 92–112 of p53 with the corresponding p73 domain resulted in a polypeptide that was resistant to E6-mediated degradation. Removal of amino acids 92–112 also resulted in a polypeptide that was resistant to E6-mediated degradation. A point mutation in the region of p53 defined by amino acids 92–112, e.g., a mutation at residue 110, rendered the mutant resistant to both Mdm2-mediated and E6-mediated degradation. A soluble synthetic or recombinant polypeptide containing the amino acid sequence of SEQ ID NO:1 blocked both Mdm2-mediated and E6-mediated degradation of p53.

EXAMPLE 4

Gene Therapy

Nucleic acids encoding a therapeutic p53 polypeptide is introduced into target cells of the patient by standard vectors and/or gene delivery systems. Suitable gene delivery systems include liposomes, receptor-mediated delivery systems, naked DNA, and viral vectors such as herpes viruses, retroviruses, and adenoviruses, among others. For example, p53 gene therapy using an adenovirus-vectored gene delivery system is a clinically safe and reliable method of directing expression of a p53 gene product in treated patients. A nucleic acid containing the nucleotide sequence, tggccctgtcatcttctgtcccttc-ccagaaaacctaccagggcagctacggtttccgtctgggc (SEQ ID NO:9), or a degenerate variant thereof is cloned into an expression vector for expression of a polypeptide which inhibits degradation of intracellular p53. A degradation-resistant p53 mutant is expressed using similar vectors. Such a mutant is encoded by the coding sequence of SEQ ID NO:8 which contains a mutation anywhere within the nucleotide sequence encoding the degradation signal, e.g., in the nucleotide sequence of SEQ ID NO:9, indicated by underlined type in Table 2 (SEQ ID NO:8). For example, the mutant has a nucleotide sequence of SEQ ID NO:8 with a mutation in the codon which encodes amino acid 110 of naturally-occurring wild type p53 which is highlighted in Table 2 (SEQ ID NO:8) by uppercase letters. The mutation is a deletion or substitution with a codon which encodes an amino acid other than arginine. For example, the mutated codon encodes an amino acid which is not positively-charged.

Vectors and gene delivery systems for expressing tumor suppressor gene products, e.g., p53, retinoblastoma protein (Rb), deleted in colorectal carcinoma protein (DCC), adenomatous polyposis protein (APC), muteated in colorectal carcinoma protein (MCC), Wilm's tumor 1 protein (WT1), neurofibromatosis type 1 protein (NF1), neurofibromatosis type 2 protein (NF2) or Hippel-Lindau Disease protein, are known in the art, e.g., those described in U.S. Pat. No. 5,700,657.

Liposome-mediated gene transfer protocols are well known in the art, e.g., Gu et al., 1997, Mol. Cell. Biochem. 172:47–57; Wang et al., 1997, Nat. Med. 3:887–893. Cationic liposomes made according to known methods (e.g., Trivedi et al., 1995, J. Neurochem. 64:2230–2238; Yu et al., 1995, Oncogene 11:1383–1388) are useful to deliver nucleic acids into target cells, e.g., cancer cells. Liposomes are not immunogenenic, and DNA delivered using liposomes is not incorporated into the genome of the recipient. Strategies to increase the efficiency of cellular transfection include condensation of plasmids into smaller particles, promotion of intracellular DNA-release form endosomes, and facilitation of plasmid nuclei-entry by nuclear localization signal.

Individuals suffering from or at risk of developing a cancer are diagnosed using standard clinical methods. Identification of individuals affected by cancer characterized by aberrant Mdm2 expression, e.g., overexpression or amplification, is also known in the art. For example Mdm2 is overexpressed in many sarcomas. Mdm2 expression is measured using standard methods, e.g., by detecting Mdm2 transcription using PCR or northern blot assays, or by detecting an Mdm2 gene product using an Mdm2-specific antibody. Other cancers in which Mdm2 is overexpressed or amplified include osteosarcoma, colon carcinoma, melanoma, choriocarcinoma, breast carcinoma, glioblastoma, neuroblastoma, and rhadomyosarcoma. Such individuals are treated by administering a p53 polypeptide (or nucleic acid encoding such a polypeptide) which inhibits degradation of endogenously-produced p53. Alternatively, a p53 mutant (or nucleic acid encoding such a mutant) which is degradation-resistant but retains tumor suppressor activity is administered.

A therapeutically effective amount is an amount which is capable of producing a medically desirable result in a treated animal. As is well known in the medical arts, dosage for any one patient depends upon many factors, including the patient's size, body surface area, age, the particular compound to be administered, sex, time and route of administration, general health, and other drugs being administered concurrently. Dosages will vary, but a preferred dosage for intravenous administration of DNA is approximately $10^6$ to $10^{22}$ copies of a DNA molecule. The compositions of the invention may be administered locally or systemically. Administration will generally be parenterally, e.g., intravenously. DNA may also be administered directly to a local target site, e.g., by biolistic delivery to a bodily tissue. For cancers in the peritoneal cavity, e.g., ovarian cancer, a therapeutic composition is delivered locally such as by peritoneal lavage, followed by intravenous administration. Intrahepatic arterial administration may be used to treat liver cancers.

EXAMPLE 5

Therapeutic Administration of a p53 Polypeptide p53 degradation such as that mediated by Mdm2 or E6 is blocked by a peptides, e.g., a synthetic or recombinant peptide, the amino acid sequence of which is derived from the degradation signal sequence of a naturally-occurring p53.

A soluble p53 polypeptide, e.g., a polypeptide containing amino acids 92–112, is administered to a mammal, e.g., a human patient, to inhibit the degradation of endogenous p53, thereby increasing tumor suppressor activity. Preferably, the inhibitory p53 polypeptide does not contain TFSDLW (SEQ ID NO:4), TFSGLW (SEQ ID NO:5), QETFSDLWKLL-PENN (SEQ ID NO:6), or PLSQETFSDLWKLLPENNV (SEQ ID NO:7).

A soluble polypeptide inhibits binding of a protein or polypeptide ligand to the degradation signal domain of endogenous p53, an event which contributes to p53 degradation.

A mutated tumor suppressor gene product which retains tumor suppressor activity but is resistant to degradation (e.g., by virtue of a mutation in a degradation signal such as SEQ ID NO:1) is administered to increase tumor suppressor activity in an individual.

Therapeutic p53-derived polypeptides or DNA encoding such polypeptides are administered using standard methods, e.g, formulated in a pharmaceutically acceptable carrier such as physiological saline or other pharmaceutically acceptable excipients. It is expected that an infusion dosage of approximately 1 to 100 μmoles of the polypeptide of the invention would be administered per kg of body weight per day.

A therapeutic p53 polypeptide has an amino acid sequence that is at least 50% identical to a naturally-occurring 53 amino acid sequence. More preferably, the sequence is at least 75% identical, more preferably 85% identical, more preferably 95% identical, more preferably 99% identical, and most preferably 100% identical to a naturally-occurring p53 sequence. Preferably, the non-identical residues are conservative amino acid substitutions.

Nucleotide and amino acid comparisons are carried out using the Lasergene software package (DNASTAR, Inc., Madison, Wis.). The MegAlign module used was the Clustal V method (Higgins et al., 1989, CABIOS 5(2):151–153). The parameter used were gap penalty 10, gap length penalty 10.

Inhibitory p53 fragments to be administered are at least 50% identical to a naturally occurring p53 sequence and have degradation inhibitory activity. Degradation-resistant p53 mutants are at least 50% identical to the full-length wild type naturally-occurring p53 sequence and have at least 50% of the transcriptional activity associated with a wild type p53.

A p53 polypeptide for therapeutic administration is substantially pure. Polypeptides are "substantially pure" when they are within preparations that are at least 60% by weight (dry weight) the compound of interest. Preferably, the preparation is at least 75%, more preferably at least 90%, and most preferably at least 99%, by weight the compound of interest. Purity is measured by any appropriate standard method, e.g., by column chromatography, polyacrylamide gel electrophoresis, or HPLC analysis. For example, the inhibitory peptide is made recombinantly or using standard amino acid synthesis technology.

To render the therapeutic peptides less susceptible to cleavage by peptidases, the peptide bonds of a peptide are replaced with an alternative type of covalent bond (a "peptide mimetic"). Replacement of a peptide bond particularly sensitive to proteolytic cleavage with a noncleavable bond will render the resulting peptide more stable and thus, more useful as a therapeutic. Such mimetics, and methods of incorporating them into polypeptides, are well known in the art. Similarly, the replacement of an L-amino acid residue with a D-amino acid is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

Organic molecules which are modeled to achieve the same or similar structure as a p53 inhibitory peptide are also useful to inhibit p53 degradation. The degradation inhibitory activity of such molecules is identified using the p53 degradation assays described herein.

Therapeutic compositions are administered to a patient systemically or locally by any appropriate method for the particular compound, e.g., orally, intravenously, parenterally, transdermally, transmucosally, by inhalation, or by surgery or implantation at or near the site where the effect of the compound is desired (e.g., with the compound being in the form of a solid or semi-solid biologically compatible and resorbable matrix). Targeted delivery of a therapeutic polypeptide is enhanced by linking the polypeptide to an anti-Mdm2 or anti-E6 antibody or antibody fragment. Delivery of inhibitory polypeptides by either anti-Mdm2 (e.g., Ab-1, Oncogene Sciences) or anti-E6 antibody-tagged liposome-mediate transfer selectively kills tumor cells while having little or no detrimental effect on normal, i.e., non-cancerous cells. Conjugation of antibodies to liposomes to make a delivery vehicle ("immunoliposomes") is well known in the art, e.g., described by Torchilin et al., 1992, FASEB J. 6:2716–2719; Bondas et al., 1999, International J. of Pharmaceutics 181:79–93; Tana et al., 1998, Japanese J. of Cancer Res. 89:1201–1211; or Koning et al., 1999, Biochimica et Biophysica Acta 1420:153–167.

Therapeutic doses are determined specifically for each compound (e.g., a polypeptide composition or organic molecule composition), most being administered within the range of 0.001 to 100.0 mg/kg body weight, or within a range that is clinically determined to be appropriate by one skilled in the art.

EXAMPLE 6

DNA Damage Induced Accumulation of Tumor Suppressors

A polypeptide containing a domain defined by amino acids 92–112 of p53 (SEQ ID NO:1) is also important for DNA-damage induced accumulation of p53. DNA encoding a polypeptide with this sequence linked to DNA encoding other tumor suppressors which bind Mdm2 such as a retinoblastoma tumor suppressor gene product (Rb-1) or alternate reading frame product (ARF) encodes a gene product which accumulates in the cell under conditions of DNA damage. For example, a DNA construct encoding a SEQ ID NO:1/Rb or SEQ ID NO:1/ARF fusion polypeptide is introduced into target cells of a patient such as a cancer patient. When the patient undergoes radiation or chemotherapy, the DNA damage resulting from the therapy induces accumulation of the fusion gene product in the cells of the patient, which results in increased tumor suppressor activity and better clinical outcome of the patient.

Other embodiments are within the following claims.

What is claimed is:

1. A substantially pure polypeptide consisting of the amino acid sequence of SEQ ID NO:1.

2. A degradation-resistant p53 polypeptide, wherein said polypeptide comprises amino acids 1–91 and 113–393 of SEQ ID NO:3 and does not comprise SEQ ID NO:1 (aa 92–112).

3. A degradation-resistant p53 polypeptide, wherein said polypeptide comprises amino acids 1–109 and 111–393 of SEQ ID NO:3 and wherein the amino acid at position 110 of said polypeptide is not positively charged.

4. The polypeptide of claims 3, wherein the amino acid at position 110 is alanine.

5. A degradation-resistant p53 polypeptide, wherein said polypeptide is a p53–p73 chimera comprising amino acids 1–91 and 113–393 of SEQ ID NO:3 and amino acids 105–131 of SEQ ID NO:10.

6. A degradation-resistant p53 polypeptide, wherein said polypeptide is a p53–p73 chimera comprising amino acids 1–45 and 113–393 of SEQ ID NO:3 and amino acids 55–131 of SEQ ID NO:10.

7. A degradation-resistant p53 polypeptide, wherein said polypeptide is a p53–p73 chimera comprising amino acids 1–290 of SEQ ID NO:3 and amino acids 310–495 of SEQ ID NO: 10.

* * * * *

SEQUENCE LISTING

<160> NUMBER OF SEQ ID NOS: 10

<210> SEQ ID NO 1
<211> LENGTH: 21
<212> TYPE: PRT
<213> ORGANISM: Homo sapiens

<400> SEQUENCE: 1

Pro Leu Ser Ser Ser Val Pro Ser Gln Lys Thr Tyr Gln Gly Ser Tyr
1               5                   10                  15

Gly Phe Arg Leu Gly
            20

<210> SEQ ID NO 2
<211> LENGTH: 21
<212> TYPE: PRT

<213> ORGANISM: Homo sapiens
<220> FEATURE:
<221> NAME/KEY: VARIANT
<222> LOCATION: (19)
<223> OTHER INFORMATION: Wherein Xaa is any amino acid.

<400> SEQUENCE: 2

```
Pro Leu Ser Ser Val Pro Ser Gln Lys Thr Tyr Gln Gly Ser Tyr
 1               5                  10                  15

Gly Phe Xaa Leu Gly
            20
```

<210> SEQ ID NO 3
<211> LENGTH: 393
<212> TYPE: PRT
<213> ORGANISM: Homo sapiens

<400> SEQUENCE: 3

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Arg Val Ala Pro Ala Pro Ala Thr Pro
 65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300
```

-continued

```
Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:Protein
      fragment not in inhibitory p53 polypeptide

<400> SEQUENCE: 4

Thr Phe Ser Asp Leu Trp
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:Protein
      fragment not in inhibitory p53 polypeptide

<400> SEQUENCE: 5

Thr Phe Ser Gly Leu Trp
 1               5

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence:Protein
      fragment not in inhibitory p53 polypeptide

<400> SEQUENCE: 6

Gln Glu Thr Phe Ser Asp Leu Trp Lys Leu Leu Pro Glu Asn Asn
 1               5                  10                  15

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence:Protein
      fragment not in inhibitory p53 polypeptide

<400> SEQUENCE: 7

Pro Leu Ser Gln Glu Thr Phe Ser Asp Leu Trp Lys Leu Leu Pro Glu
 1               5                  10                  15

Asn Asn Val

<210> SEQ ID NO 8
<211> LENGTH: 1307
```

```
<212> TYPE: DNA
<213> ORGANISM: Homo sapiens

<400> SEQUENCE: 8
accgtccagg gagcaggtag ctgctgggct ccggggacac tttgcgttcg ggctgggagc      60
gtgctttcca cgacggtgac acgcttccct ggattggcag ccagactgcc ttccgggtca     120
ctgccatgga ggagccgcag tcagatccta gcgtcgagcc ccctctgagt caggaaacat     180
tttcagacct atggaaacta cttcctgaaa acaacgttct gtcccccttg ccgtcccaag     240
caatggatga tttgatgctg tccccggacg atattgaaca atggttcact gaagacccag     300
gtccagatga agctcccaga atgccagagg ctgctccccg cgtggcccct gcaccagcga     360
ctcctacacc ggcggcccct gcaccagccc ctcctggcc cctgtcatct tctgtccctt      420
cccagaaaac ctaccagggc agctacggtt tccgtctggg cttcttgcat tctgggacag     480
ccaagtctgt gacttgcacg tactcccctg ccctcaacaa gatgttttgc caactggcca     540
agacctgccc tgtgcagctg tgggttgatt ccacaccccc gcccggcacc cgcgtccgcg     600
ccatggccat ctacaagcag tcacagcaca tgacggaggt tgtgaggcgc tgccccacc      660
atgagcgctg ctcagatagc gatggtctgg cccctcctca gcatcttatc cgagtggaag     720
gaaatttgcg tgtggagtat ttggatgaca gaaacacttt tcgacatagt gtggtggtgc     780
cctatgagcc gcctgaggtt ggctctgact gtaccaccat ccactacaac tacatgtgta     840
acagttcctg catgggcggc atgaaccgga ggcccatcct caccatcatc acactgaag      900
actccagtgg taatctactg ggacggaaca gctttgaggt gcgtgtttgt gcctgtcctg     960
ggagagaccg gcgcacagag gaagagaatc tccgcaagaa aggggagcct caccacgagc    1020
tgccccagg gagcactaag cgagcactgc ccaacaacag cagctcctct ccccagccaa    1080
agaagaaacc actggatgga gaatatttca cccttcagat ccgtgggcgt gagcgcttcg    1140
agatgttccg agagctgaat gaggccttgg aactcaagga tgcccaggct gggaaggagc    1200
caggggggag cagggctcac tccagccacc tgaagtccaa aaagggtcag tctacctccc    1260
gccataaaaa actcatgttc aagacagaag ggcctgactc agactga                  1307

<210> SEQ ID NO 9
<211> LENGTH: 66
<212> TYPE: DNA
<213> ORGANISM: Artificial Sequence
<220> FEATURE:
<223> OTHER INFORMATION: Description of Artificial Sequence:p53
      inhibiting nucleic acid

<400> SEQUENCE: 9
tggcccctgt catcttctgt cccttcccag aaaacctacc agggcagcta cggtttccgt      60
ctgggc                                                                  66

<210> SEQ ID NO 10
<211> LENGTH: 636
<212> TYPE: PRT
<213> ORGANISM: Homo sapiens

<400> SEQUENCE: 10

Met Ala Gln Ser Thr Ala Thr Ser Pro Asp Gly Gly Thr Thr Phe Glu
  1               5                  10                  15

His Leu Trp Ser Ser Leu Glu Pro Asp Ser Thr Tyr Phe Asp Leu Pro
             20                  25                  30

Gln Ser Ser Arg Gly Asn Asn Glu Val Val Gly Gly Thr Asp Ser Ser
```

-continued

```
                35                  40                  45
Met Asp Val Phe His Leu Glu Gly Met Thr Thr Ser Val Met Ala Gln
 50                      55                  60

Phe Asn Leu Leu Ser Ser Thr Met Asp Gln Met Ser Ser Arg Ala Ala
 65                      70                  75                  80

Ser Ala Ser Pro Tyr Thr Pro Glu His Ala Ala Ser Val Pro Thr His
                 85                  90                  95

Ser Pro Tyr Ala Gln Pro Ser Ser Thr Phe Asp Thr Met Ser Pro Ala
                100                 105                 110

Pro Val Ile Pro Ser Asn Thr Asp Tyr Pro Gly Pro His His Phe Glu
                115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160

Ile Gln Ile Lys Val Ser Thr Pro Pro Pro Gly Thr Ala Ile Arg
                165                 170                 175

Ala Met Pro Val Tyr Lys Lys Ala Glu His Val Thr Asp Val Val Lys
                180                 185                 190

Arg Cys Pro Asn His Glu Leu Gly Arg Asp Phe Asn Glu Gly Gln Ser
    195                 200                 205

Ala Pro Ala Ser His Leu Ile Arg Val Glu Gly Asn Asn Leu Ser Gln
    210                 215                 220

Tyr Val Asp Asp Pro Val Thr Gly Arg Gln Ser Val Val Val Pro Tyr
225                 230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
                260                 265                 270

Ile Ile Ile Thr Leu Glu Met Arg Asp Gly Gln Val Leu Gly Arg Arg
                275                 280                 285

Ser Phe Glu Gly Arg Ile Cys Ala Cys Pro Gly Arg Asp Arg Lys Ala
    290                 295                 300

Asp Glu Asp His Tyr Arg Glu Gln Gln Ala Leu Asn Glu Ser Ser Ala
305                 310                 315                 320

Lys Asn Gly Ala Ala Ser Lys Arg Ala Phe Lys Gln Ser Pro Pro Ala
                325                 330                 335

Val Pro Ala Leu Gly Ala Gly Val Lys Lys Arg Arg His Gly Asp Glu
                340                 345                 350

Asp Thr Tyr Tyr Leu Gln Val Arg Gly Arg Glu Asn Phe Glu Ile Leu
                355                 360                 365

Met Lys Leu Lys Glu Ser Leu Glu Leu Met Glu Leu Val Pro Gln Pro
    370                 375                 380

Leu Val Asp Ser Tyr Arg Gln Gln Gln Gln Leu Leu Gln Arg Pro Ser
385                 390                 395                 400

His Leu Gln Pro Pro Ser Tyr Gly Pro Val Leu Ser Pro Met Asn Lys
                405                 410                 415

Val His Gly Gly Met Asn Lys Leu Pro Ser Val Asn Gln Leu Val Gly
                420                 425                 430

Gln Pro Pro Pro His Ser Ser Ala Ala Thr Pro Asn Leu Gly Pro Val
                435                 440                 445

Gly Pro Gly Met Leu Asn Asn His Gly His Ala Val Pro Ala Asn Gly
                450                 455                 460
```

-continued

```
Glu Met Ser Ser Ser His Ser Ala Gln Ser Met Val Ser Gly Ser His
465                 470                 475                 480

Cys Thr Pro Pro Pro Tyr His Ala Asp Pro Ser Leu Val Ser Phe
            485                 490                 495

Leu Thr Gly Leu Gly Cys Pro Asn Cys Ile Glu Tyr Phe Thr Ser Gln
            500                 505                 510

Gly Leu Gln Ser Ile Tyr His Leu Gln Asn Leu Thr Ile Glu Asp Leu
            515                 520                 525

Gly Ala Leu Lys Ile Pro Glu Gln Tyr Arg Met Thr Ile Trp Arg Gly
    530                 535                 540

Leu Gln Asp Leu Lys Gln Gly His Asp Tyr Ser Thr Ala Gln Gln Leu
545                 550                 555                 560

Leu Arg Ser Ser Asn Ala Ala Thr Ile Ser Ile Gly Gly Ser Gly Glu
                565                 570                 575

Leu Gln Arg Gln Arg Val Met Glu Ala Val His Phe Arg Val Arg His
            580                 585                 590

Thr Ile Thr Ile Pro Asn Arg Gly Gly Pro Gly Gly Gly Pro Asp Glu
        595                 600                 605

Trp Ala Asp Phe Gly Phe Asp Leu Pro Asp Cys Lys Ala Arg Lys Gln
    610                 615                 620

Pro Ile Lys Glu Glu Phe Thr Glu Ala Glu Ile His
625                 630                 635
```